US008778000B2

(12) United States Patent
Haddad et al.

(10) Patent No.: US 8,778,000 B2
(45) Date of Patent: Jul. 15, 2014

(54) ORTHOPEDIC PLATE, ORTHOPEDIC DEVICE, METHOD OF COUPLING BONE SEGMENTS, AND METHOD OF ASSEMBLING AN ORTHOPEDIC PLATE

(71) Applicant: Zimmer GMBH, Winterthur (CH)

(72) Inventors: Steven L. Haddad, Glenview, IL (US); Paul C. Bond, Chicago, IL (US)

(73) Assignee: Zimmer GmbH, Winterthur (CH)

( * ) Notice: Subject to any disclaimer, the term of this patent is extended or adjusted under 35 U.S.C. 154(b) by 0 days.

(21) Appl. No.: 13/767,462

(22) Filed: Feb. 14, 2013

(65) Prior Publication Data

US 2014/0163622 A1 Jun. 12, 2014

Related U.S. Application Data

(63) Continuation of application No. 13/708,213, filed on Dec. 7, 2012.

(60) Provisional application No. 61/569,052, filed on Dec. 9, 2011.

(51) Int. Cl.
*A61B 17/60* (2006.01)
*A61F 5/04* (2006.01)

(52) U.S. Cl.
USPC .......................................... 606/290

(58) Field of Classification Search
USPC .................. 606/280–299, 268–269
See application file for complete search history.

(56) References Cited

U.S. PATENT DOCUMENTS

| 1,088,046 | A | * | 2/1914 | Turner | 411/403 |
| 2,445,978 | A | * | 7/1948 | Stellin | 411/404 |
| 3,331,274 | A | * | 7/1967 | Walton | 411/403 |
| 4,388,921 | A | * | 6/1983 | Sutter et al. | 606/71 |
| 4,566,448 | A | | 1/1986 | Rohr, Jr. | |
| 5,366,330 | A | * | 11/1994 | Cosenza | 411/405 |
| 5,514,138 | A | * | 5/1996 | McCarthy | 606/65 |
| 5,578,034 | A | * | 11/1996 | Estes | 606/281 |
| 5,598,753 | A | * | 2/1997 | Lee | 81/460 |
| 5,607,426 | A | * | 3/1997 | Ralph et al. | 606/287 |
| 5,954,722 | A | | 9/1999 | Bono | |
| 6,235,033 | B1 | | 5/2001 | Brace et al. | |

(Continued)

FOREIGN PATENT DOCUMENTS

| WO | WO03084412 | 10/2003 |
| WO | WO2010132252 | 11/2010 |
| WO | WO-2013086321 | 6/2013 |

OTHER PUBLICATIONS

International Search Report of PCT/US2012/068449, Mailed on Mar. 19, 2013, 4 pages.

(Continued)

*Primary Examiner* — Matthew Lawson
*Assistant Examiner* — Zade Coley
(74) *Attorney, Agent, or Firm* — Schwegman Lundberg & Woessner, P.A.

(57) ABSTRACT

An orthopedic plate comprising, a frame portion and a bearing rotatably coupled with the frame portion, wherein the bearing defines an opening configured to receive a fastener for fastening the orthopedic plate to a body, wherein the bearing includes an outer surface that is eccentric to the opening such that a position of the opening with respect to the frame portion is adjustable as the bearing rotates.

16 Claims, 14 Drawing Sheets

(56) References Cited

U.S. PATENT DOCUMENTS

| | | | |
|---|---|---|---|
| 6,241,736 B1* | 6/2001 | Sater et al. | 606/104 |
| 6,302,632 B1* | 10/2001 | Lin | 411/404 |
| 6,319,270 B1* | 11/2001 | Grafton et al. | 606/232 |
| 6,355,038 B1* | 3/2002 | Pisharodi | 606/300 |
| 6,648,891 B2 | 11/2003 | Kim | |
| 6,695,846 B2* | 2/2004 | Richelsoph et al. | 606/71 |
| 7,001,389 B1* | 2/2006 | Navarro et al. | 606/71 |
| 7,771,458 B2* | 8/2010 | Biedermann et al. | 606/289 |
| 7,785,327 B1* | 8/2010 | Navarro et al. | 606/71 |
| 7,833,254 B2* | 11/2010 | Celli et al. | 606/295 |
| 8,287,575 B2* | 10/2012 | Murner et al. | 606/287 |
| 2002/0058939 A1* | 5/2002 | Wagner et al. | 606/61 |
| 2003/0171754 A1* | 9/2003 | Del Medico | 606/69 |
| 2003/0187440 A1* | 10/2003 | Richelsoph et al. | 606/61 |
| 2003/0187442 A1* | 10/2003 | Richelsoph et al. | 606/70 |
| 2004/0127896 A1* | 7/2004 | Lombardo et al. | 606/61 |
| 2004/0127899 A1* | 7/2004 | Konieczynski et al. | 606/69 |
| 2005/0043736 A1* | 2/2005 | Mathieu et al. | 606/73 |
| 2005/0049593 A1* | 3/2005 | Duong et al. | 606/69 |
| 2005/0059970 A1* | 3/2005 | Kolb | 606/69 |
| 2005/0228386 A1* | 10/2005 | Ziolo et al. | 606/69 |
| 2005/0288668 A1* | 12/2005 | Brinkhaus | 606/61 |
| 2006/0235402 A1* | 10/2006 | Celli et al. | 606/69 |
| 2008/0243192 A1* | 10/2008 | Jacene et al. | 606/290 |
| 2008/0288001 A1* | 11/2008 | Cawley et al. | 606/295 |
| 2009/0036931 A1 | 2/2009 | Pech et al. | |
| 2009/0082814 A1* | 3/2009 | Bickley et al. | 606/286 |
| 2009/0149888 A1* | 6/2009 | Abdelgany | 606/286 |
| 2009/0210011 A1 | 8/2009 | Den Hartog et al. | |
| 2010/0249853 A1* | 9/2010 | Celli et al. | 606/289 |
| 2011/0144700 A1* | 6/2011 | Konieczynski et al. | 606/289 |
| 2011/0270320 A1* | 11/2011 | Oh et al. | 606/290 |
| 2012/0022600 A1* | 1/2012 | Overes et al. | 606/286 |
| 2013/0150900 A1 | 6/2013 | Haddad et al. | |

OTHER PUBLICATIONS

Instruction Sheet No. 9060049A dated Sep. 16, 1998 by "Room Additions—Furniture from the Heartland," 423 Hopewell Road, Waverly, Ohio, 45690, 8 pages.

"U.S. Appl. No. 13/708,213, Preliminary Amendment filed Jan. 24, 2013", 7 pgs.

* cited by examiner

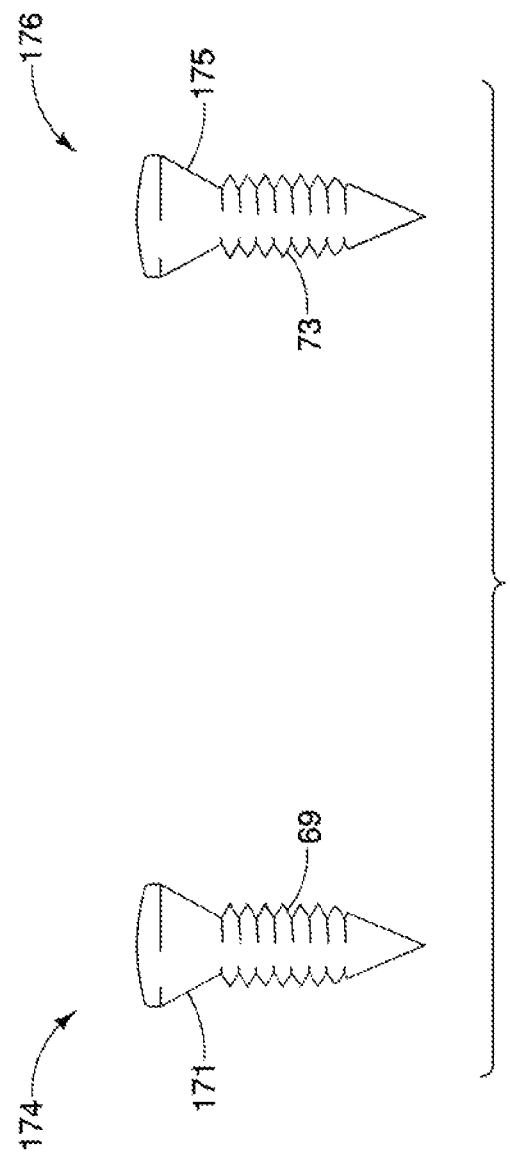

ORTHOPEDIC PLATE, ORTHOPEDIC DEVICE, METHOD OF COUPLING BONE SEGMENTS, AND METHOD OF ASSEMBLING AN ORTHOPEDIC PLATE

CROSS-REFERENCE TO RELATED APPLICATION

This application is a Continuation of U.S. patent application Ser. No. 13/708,213, filed Dec. 7, 2012, which claims the benefit of U.S. Provisional Patent Application No. 61/569,052, filed Dec. 9, 2011; the entire contents of both applications are incorporated herein by reference.

FIELD

The present disclosure relates generally to devices for and methods of repairing bones and/or bone joints and methods of assembling said devices. More specifically, the disclosure relates to an orthopedic plate or an orthopedic device for coupling bone segments, a method of doing the same, and a method of assembling an orthopedic plate.

BACKGROUND

The statements in this section merely provide background information related to the present disclosure and may not constitute prior art.

When treating bone fractures, where a single bone is broken into two or more bone segments, a medical professional often desires to promote union between the two or more bone segments. The same is the case when a medical professional desires to cause or help to cause bone fusions, i.e., uniting two bones into one bone by eliminating a joint therebetween. When promoting union of two or more bone segments via standard biologic healing, whether the bone segments are pieces of a single bone or whether the bone segments are separate bones, it is often desirable to have precise alignment of bone segments and complete or substantially complete contact between the involved surfaces.

Alignment of the bone segments is desirable not only to enhance a union of bone segments, but also to prevent or reduce the likelihood of subsequent deformity following union. If malalignment is created at the time of fracture fixation, the ability of the bones to heal may be compromised and, if union is achieved, an alteration in force distribution may occur across formerly precisely balanced joints that may lead to increased contact stresses and subsequent arthritis. Joints often require precise balance to prevent portions of the cartilage from accelerated wear (wearing away the cartilage with repetitive cycles of loading), which may lead to early onset arthritis.

Thus, under the above-mentioned circumstances, the ability of the medical professional to achieve an outcome that both the patient and clinician approve of is often directly related to the quality of the reduction of the bone segments.

Traditionally, medical professionals, such as orthopedic surgeons, use plate fixation to hold the various bone segments into the correct position while they heal. The plates themselves are typically primarily alignment devices. While they may provide some element of structural support, if the fracture or fusion does not heal (nonunion), the plate and screw construct often eventually fails due to cyclic loading.

Dynamic compression plates have been used by medical professionals to attempt to promote biologic healing by creating a more complete and flush bond between bone segments. One type of dynamic compression plate includes oblong, rather than circular, holes to allow the medical professional to compress the fracture/fusion site by placing the screw against the side of the hole that is farthest from the fracture/fusion site. This type of compression plate is utilized with fasteners, such as screws, having a cone-shaped head with its largest diameter at the top of the fastener head. As the medical professional tightens the screw against the plate, the screw head engages the far end of the plate screw hole. Then, as the medical professional continues to tighten the fastener, the cone-shaped fastener head pushes the plate in a direction away from the fracture/fusion site as long as two conditions are met: (1) the bottom side of the plate is in contact with the bone to prevent the plate from moving downward as the fastener moves downward, and (2) the other end of the plate is secured to the bone on the opposite side of the fracture/fusion site.

The first of the above-mentioned conditions, namely that the bottom side of the plate is in contact with the bone while the fastener is being driven downward into the bone, may diminish the plate's effectiveness or render the plate unusable with bones that are not relatively flat. For example, as the medical professional tightens a fastener and causes the plate to contact an uneven bone surface, the bone may become distorted or otherwise damaged. Distortion of the fracture or fusion site may alter the alignment of said site or may limit the contact surface area between the bone segments. In either case, the desired goal of anatomic restoration of the bone or fusion site with maximal surface area available for healing may not be achieved. As a result, this type of dynamic compression plate may be undesirable for use with curved or uneven bone surfaces.

This type of dynamic compression plate may also be undesirable because the amount of compression is dependent on the screw height. In other words, the position of the plate along a first axis is dependent on the position of the fastener along a second axis that is generally perpendicular to the first axis. The dependent relationship between the plate and the screw height may not be desirable because it may prevent the medical professional from creating a desired compression force acting on the bone segments while the fasteners are at their desired positions.

Therefore, it is desirous to provide an orthopedic plate, device, or method that can be used with bone segments having various shapes while allowing dynamic compression of multiple bone segments and/or that can be used to create a desired compression force acting on the bone segments while the fasteners are at their desired positions.

SUMMARY

In overcoming the limitations and drawbacks of the prior art, the present orthopedic plate, device, and methods facilitate and/or provide dynamic compression between multiple bone segments.

In one aspect, an orthopedic plate is provided, comprising a frame portion, and a bearing rotatably coupled with the frame portion, wherein the bearing defines an opening configured to receive a fastener for fastening the orthopedic plate to a body, wherein the bearing includes an outer surface that is eccentric to the opening such that a position of the opening with respect to the frame portion is adjustable as the bearing rotates, and wherein the bearing includes at least a first ridge that is an anchoring ridge and a second ridge that is a locking ridge.

The anchoring ridge may have an inner diameter that is smaller than an inner diameter of the locking ridge. Furthermore, the anchoring ridge may be configured to mate with a first set of fastener threads and the locking ridge is configured to mate with a second set of fastener threads. The bearing may be configured to expand in diameter when the second set of fastener threads is received within the locking ridge.

The anchoring ridge may be configured to mate with a first set of fastener threads and the locking ridge is configured to receive a locking head. The bearing may be configured to expand in diameter when the locking head is received within the locking ridge.

The orthopedic plate may also include a second bearing rotatably coupled with the frame portion, wherein the second bearing defines a second opening configured to receive a second fastener for further fastening the orthopedic plate to a body, wherein the second bearing includes an outer surface that is eccentric to the second opening.

In another aspect an orthopedic plate is provided, having a frame portion and a bearing rotatably coupled with the frame portion, wherein the bearing defines an opening configured to receive a fastener for fastening the orthopedic plate to a body, wherein the bearing includes an outer surface that is eccentric to the opening such that a position of the opening with respect to the frame portion is adjustable as the bearing rotates and wherein the bearing includes at least one key hole to facilitate rotation of the bearing with respect to the frame portion.

The bearing may include at least two key holes to facilitate rotation of the bearing with respect to the frame portion. The bearing may also be configured to facilitate rotation of the bearing with respect to the frame portion while the fastener is received within the opening.

In yet another aspect, an orthopedic device is provided, configured to facilitate cutting at least one of first and second bone segments of a body and comprising a jig configured to be secured to the first and second bone segments of the body and a cutting guide coupled with the jig, wherein a position of the cutting guide with respect to the jig is adjustable along a first axis.

In another aspect, an orthopedic device is configured to facilitate coupling first and second bone segments of a body and comprising a jig having a first arm configured to be secured to the first bone segment, a second arm configured to be secured to the second bone segment, and a jig adjustment mechanism configured to adjust the position of the first arm with respect to the second arm to adjust a distance between the first and second bone segments.

In yet another aspect, a method of coupling first and second bone segments of a body is provided, comprising coupling a first arm of a jig with the first bone segment and coupling a second arm of the jig with the second bone segment, coupling a cutting guide with the jig to facilitate cutting at least one of the first and second bone segments, cutting at least one of the first and second bone segments, decoupling the cutting guide from the jig, coupling a plate holding mechanism with the jig, coupling an orthopedic plate with the plate holding mechanism, adjusting the plate holding mechanism so as to move the orthopedic plate into a desired position with respect to the first and second bone segments, securing a first portion of the orthopedic plate to the first bone segment and securing a second portion of the orthopedic plate to the second bone segment, adjusting at least one of the following: a position of at least one of the first and second arms of the jig so as to adjust a distance between the first and second bone segments and a plate adjusting mechanism to adjust a distance between the first and second bone segments.

Further objects, features and advantages of the orthopedic plate, device, and method will become readily apparent to persons skilled in the art after a review of the following description, with reference to the drawings and claims that are appended to and form a part of this specification.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 27 is an alternative embodiment of a fastener configured to couple an orthopedic plate to one or more bone segments.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
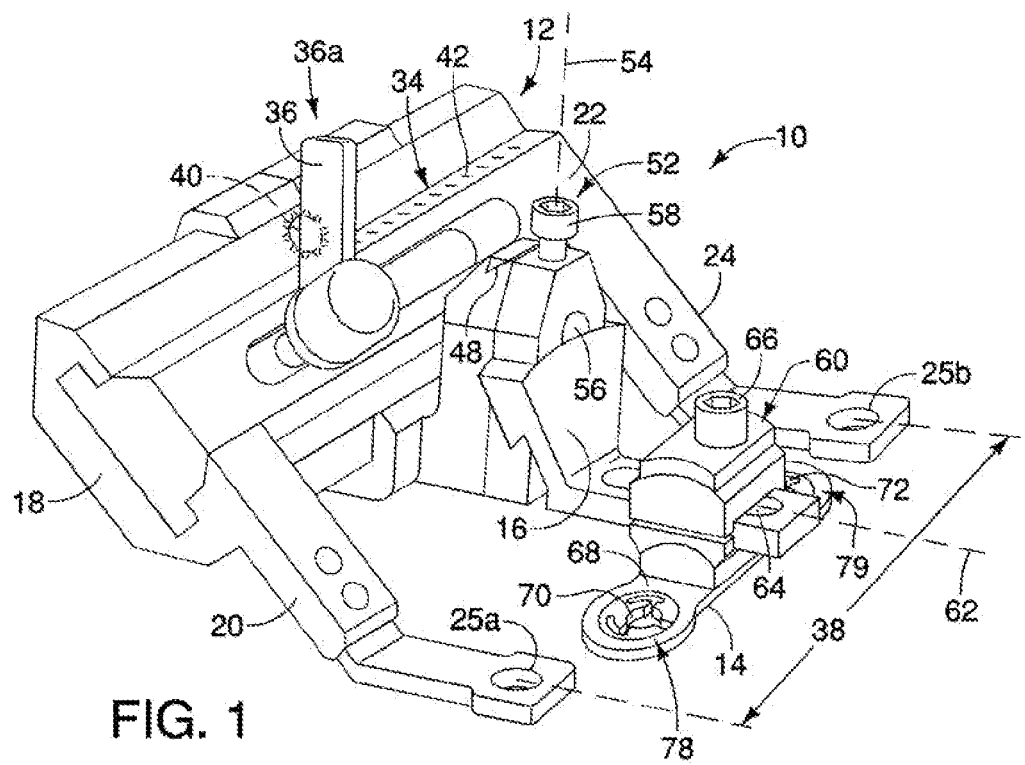
FIG. 1 shows an isometric view of an orthopedic device embodying principles of the present invention and having a jig with first and second arms and an orthopedic plate.

Referring now to the drawings, FIG. 1 shows an orthopedic device 10 for coupling bone segments of a patient's body. The orthopedic device 10 includes a jig 12, an orthopedic plate 14, and a plate holding mechanism 16. Although these components are shown being used with each other, many or all of the components may be used independently of each other. For example, a medical professional may choose to use the orthopedic plate 14 without using the jig 12 or may choose to use the jig 12 with another orthopedic plate or another device altogether.

The jig 12 shown in the figures is coupled with the patient's body to facilitate installation of the orthopedic plate 14. The jig 12 shown in the figures includes a first portion 18 having a first arm 20 that is able to be coupled with the patient's body and a second portion 22 having a second arm 24 that is also able to be coupled with the patient's body.

Figure 7:
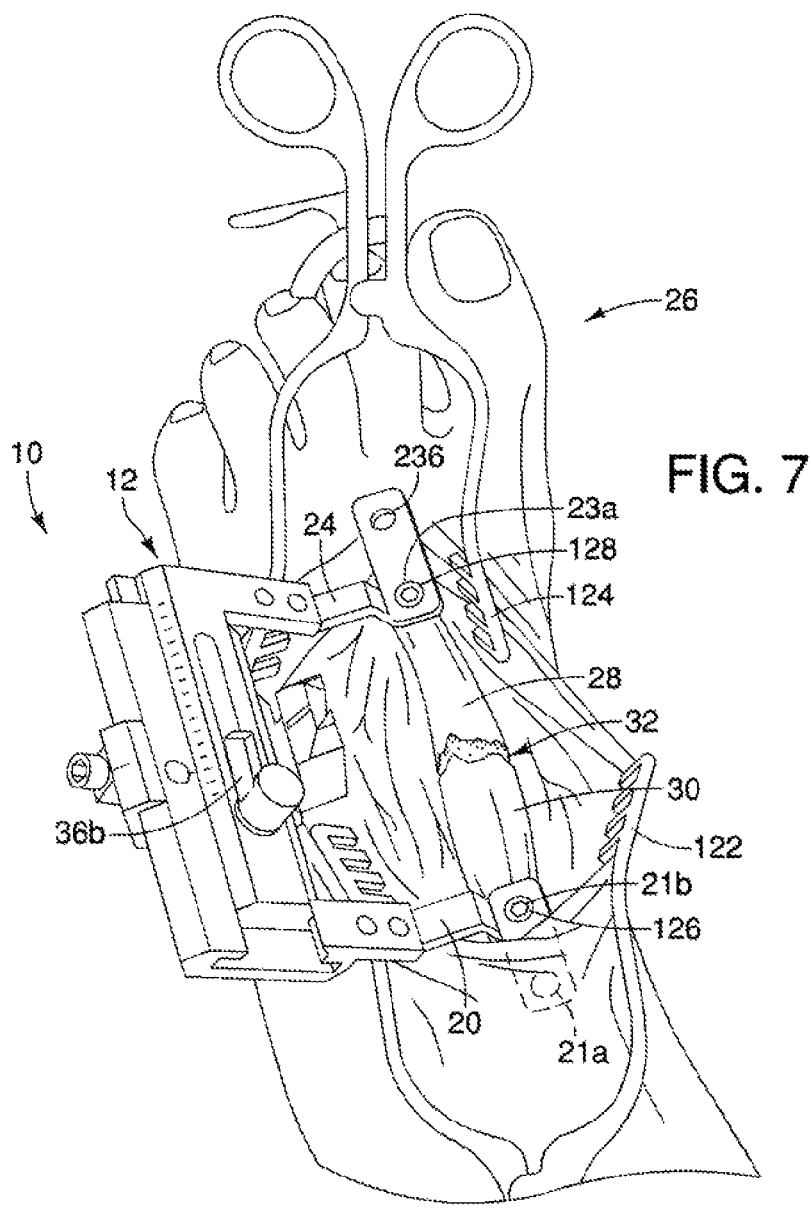
FIG. 7 is an isometric view of an alternative embodiment of an orthopedic device coupled with first and second bone segments of a patient's body.

For example, FIG. 7 shows a patient's body 26, particularly a patient's foot, having a first bone segment 28 and a second bone segment 30 that have been separated via a fracture 32. In the embodiment of the jig 12 shown in FIG. 7, the first and second arms 20, 24 each have two fastener holes 21a, 21b, 23a, 23b that may be used to secure the jig 12 to the bone segments, whereas the first and second arms 20, 24 of the jig 12 shown in FIG. 1 each include one fastener hole 25a, 25b. Although the figures focus on the foot portion of the patient's body 26, the present invention may be used with any suitable portion of a patient's body, such as the hands, ankles, wrists, legs, arms, oral or maxillofacial areas, or any other portion of a patient's body. The patient shown in the drawings is human, but the devices and methods disclosed herein may also be used on animals, such as through veterinarian medicine, and thus the term "medical professional" includes all types of medicine, including veterinarian medicine.

Referring to FIG. 7-16, although these figures show first and second bone segments 28, 30 of a metatarsal bone that have been separated via a fracture 32, the present invention may be used with any suitable injury, condition, disease, malady, or weakness to a patient's body, such as a fracture, fusion, crack, or damaged joint. The term "bone segments" may refer to two portions of a single bone or two different bones. The metatarsal bone shown in the figures is, for illustrative purposes, longer and extends more proximal than a typical metatarsal bone in a normal adult patient. Also, for illustrative purposes, other bones of the patient's foot are not shown. If the jig 12 was used for a fusion application, rather than a fracture, in a similar area of a patient's foot, then the first and second arms of the jig likely would be secured to a metatarsal distally and a cuneiform proximally. However, as discussed above, the orthopedic device 10 may be used with any suitable bone segments.

Referring to FIGS. 1-4, the second portion 22 of the jig 12 is slidably received within the first portion 18 so that the respective portions 18, 22 are movable with respect to each other. The first and second portions 18, 22 shown in the figures further include a jig adjustment mechanism 34 and a locking key 36 for adjusting a distance 38 between the first arm 20 and the second arm 24 of the jig 12. The locking key includes a locked position 36a (FIGS. 1-4, 8-10, 12-15), in which the first and second portions 18, 22 of the jig 12 are movable with respect to each other, and an unlocked position 36b (FIGS. 7 and 11), in which the first and second portions 18, 22 of the jig 12 are not movable with respect to each other. The jig 12 shown in the figures also includes a gear 40 and track 42, such as a rack and pinion, that cooperate to define the jig adjustment mechanism 34, but any other suitable adjustment mechanism may be used. The gear 40 in the figures is located within a cavity defined by the jig first portion 18 and is accessible from outside the jig 12 via a key hole 44 in the jig 12. The orthopedic device 10 further includes an adjustment key 46 (FIGS. 4, 11) configured to be inserted into the key hole 44 (FIGS. 2, 8-10) and rotate the gear 40, thereby adjusting the distance 38 between the first and second arms 20, 24. When the jig 12 is coupled with the first and second bone segments 28, 30, by turning the adjustment key 46, a medical professional is able to adjust the relative position of the first and second bone segments 28, 30 with respect to each other. As a result, a medical professional is able to use the jig 12 to cause the first and second bone segments to dynamically compress, or cause the bone segments 28, 30 to come into contact with each other, and potentially promote biological healing.

Figure 2:
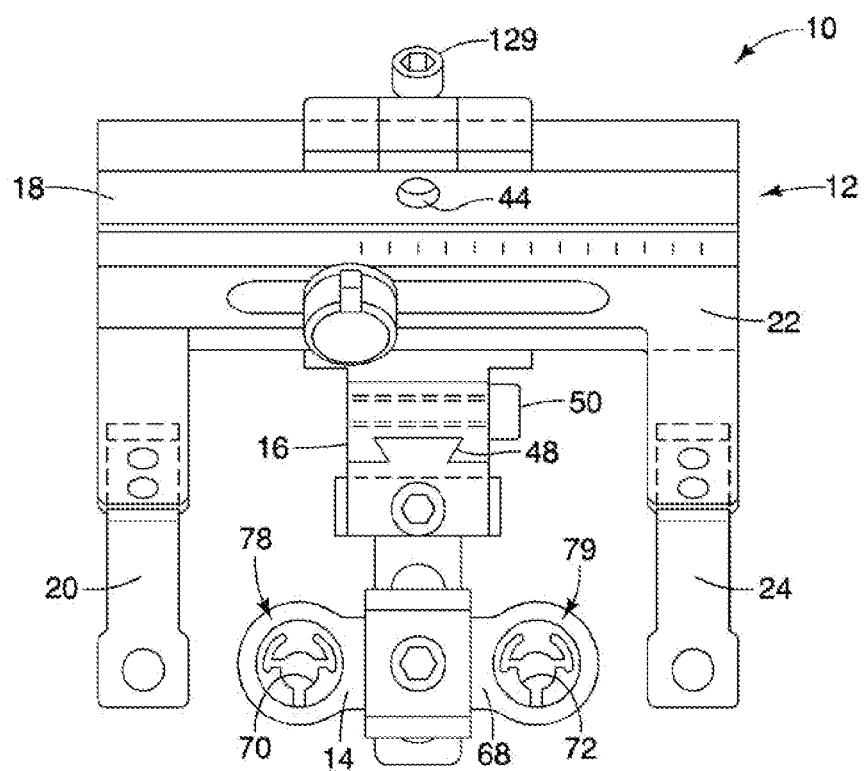
FIG. 2 is a top view of the orthopedic device shown in FIG. 1.
Figure 3:
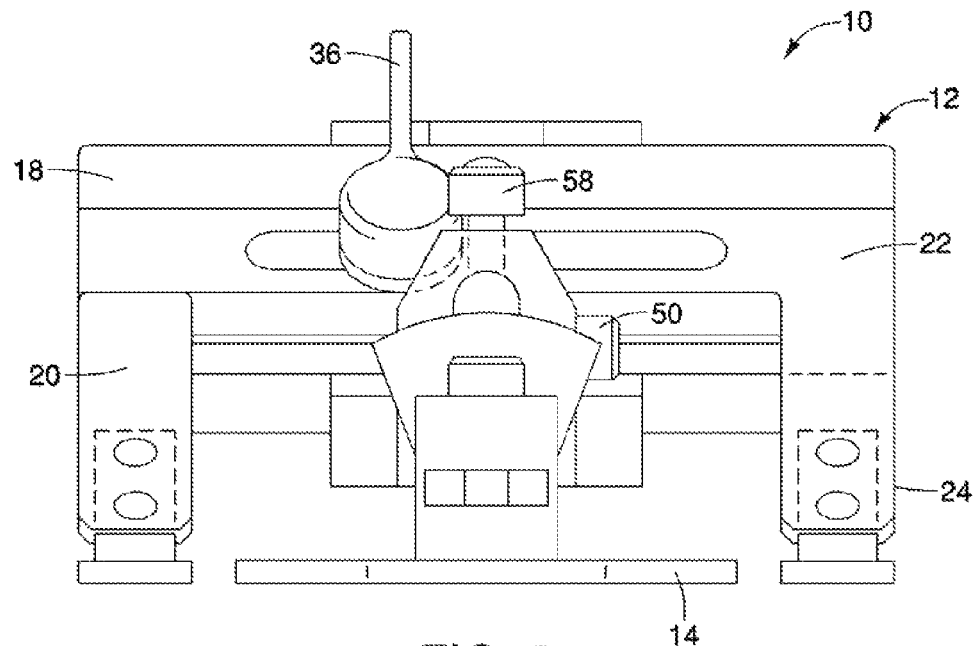
FIG. 3 is a front view of the orthopedic device shown in FIG. 1.
Figure 4:
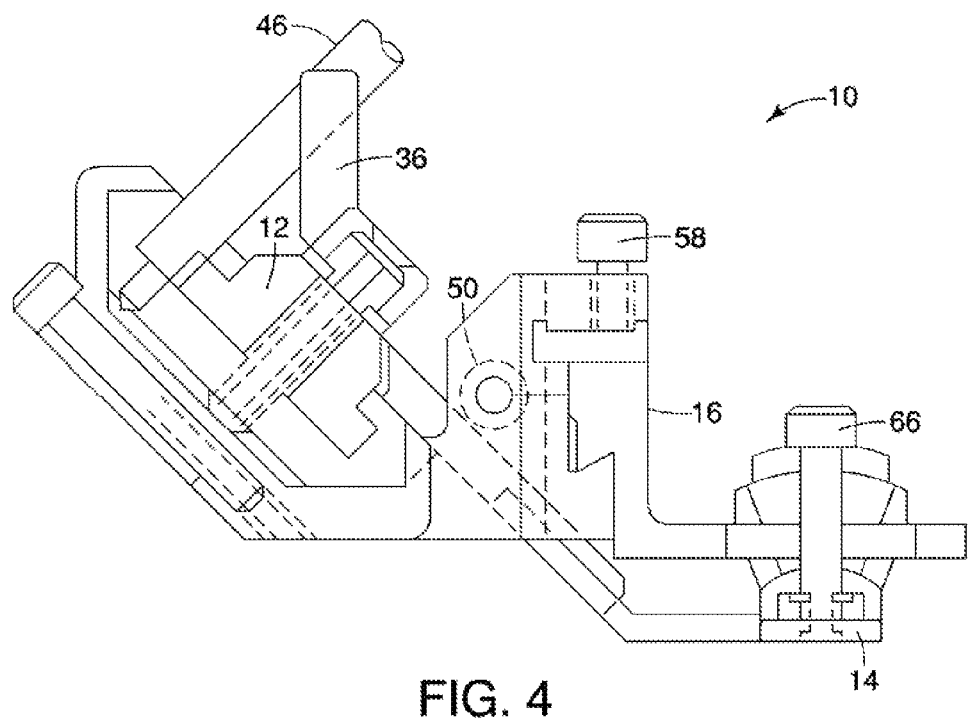
FIG. 4 is a side view of the orthopedic device shown in FIG. 1.

As best shown in FIGS. 1 and 2, the plate holding mechanism 16 is coupled to the jig 12 via a tab-slot connection 48 and securing pin 50 (FIG. 2) which secures the tab-slot connection 48. The plate holding mechanism 16 further includes a vertical adjustment mechanism 52 configured to adjust the position of the orthopedic plate 14 along a y-axis 54 (FIG. 1). For example, the vertical adjustment mechanism 52 shown in the figures includes a tab-slot connection 56 and securing pin 58 securing the tab-slot connection 56 (FIG. 1). The plate holding mechanism 16 further includes a horizontal adjustment mechanism 60 configured to adjust the position of the orthopedic plate 14 along an x-axis 62 (FIG. 1). For example, the horizontal adjustment mechanism 60 shown in the figures includes a tab-slot connection 64 and securing pin 66 securing the tab-slot connection 64 (FIG. 1). By using the vertical adjustment mechanism 52 and the horizontal adjustment mechanism 60, a medical professional is able to adjust the position of the orthopedic plate 14 with respect to the first and second bone segments 28, 30 so as to properly align the orthopedic plate 14 before coupling it with the bone segments 28, 30. In an alternative embodiment, the vertical adjustment mechanism and the horizontal adjustment mechanism include gear and track mechanisms such as the rack and pinion mechanism discussed with respect to the jig adjustment mechanism 34.

Figure 5A:
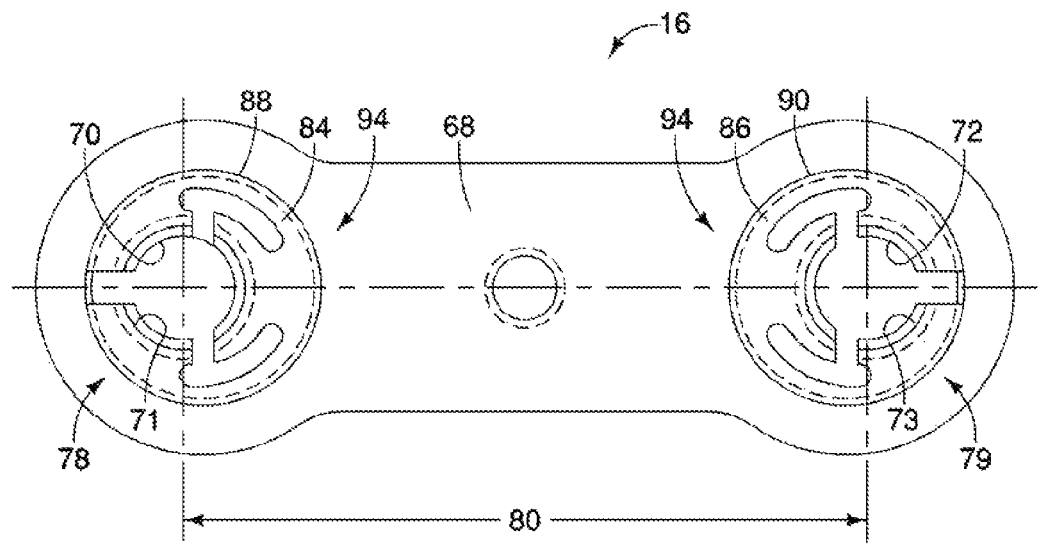
FIG. 5a is a top view of the orthopedic plate shown in FIG. 1 where first and second bearings of the orthopedic plate are each in a non-compressed position.
Figure 5B:
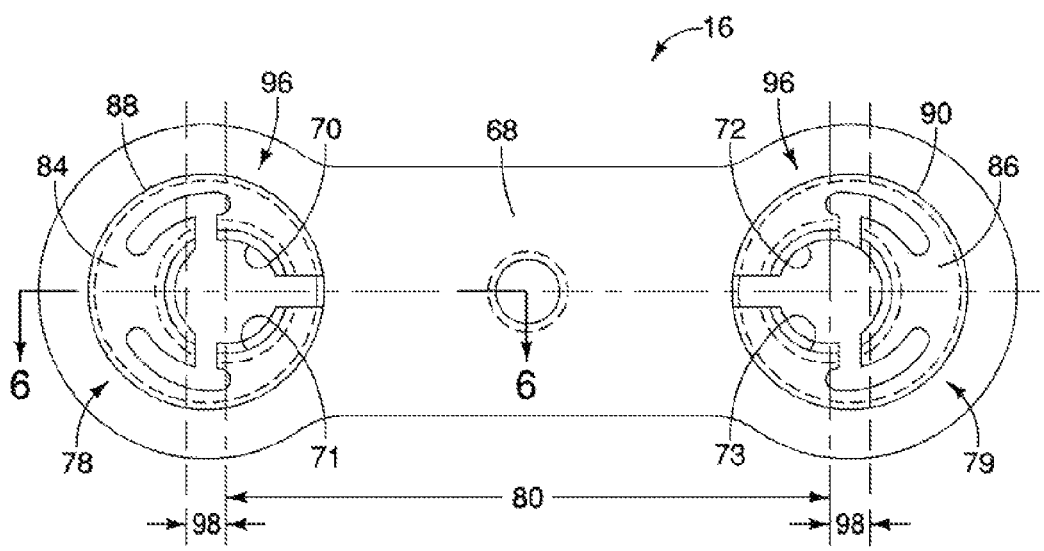
FIG. 5b is a top view of the orthopedic plate shown in FIG. 1 where the first and second bearings of the orthopedic plate are each in a compressed position.

As is best shown in FIGS. 5a and 5b, the orthopedic plate 14 includes a frame portion 68 and first and second plate adjustment mechanisms 78, 79 that are each configured to adjust a distance 80 (FIG. 16) between first and second fasteners 74, 76 (FIGS. 15, 16), respectively. The plate adjustment mechanisms 78, 79 shown in the figures include a first bearing 84 that is rotatable with respect to the frame portion 68 and a second bearing 86 that is rotatable with respect to the frame portion 68.

The orthopedic plate 14 shown in the figures defines a first opening 70 and a second opening 72 that are configured to receive the first and second fasteners 74, 76, to couple the orthopedic plate 14 to the first and second bone segments 28, 30. The distance 80 is measured at the center of each of the fasteners 74, 76 and is therefore, in the embodiments shown in the figures, the same distance as that measured from the respective centers of each of the openings 70, 72 (FIGS. 5a, 5b).

Figure 6:
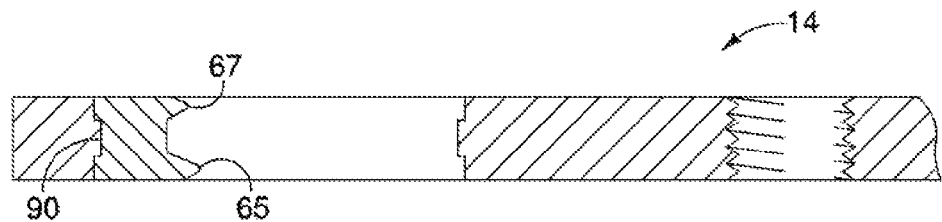
FIG. 6 is a cross-sectional view of the orthopedic plate shown in FIG. 5b taken along line 6-6.
Figure 22:
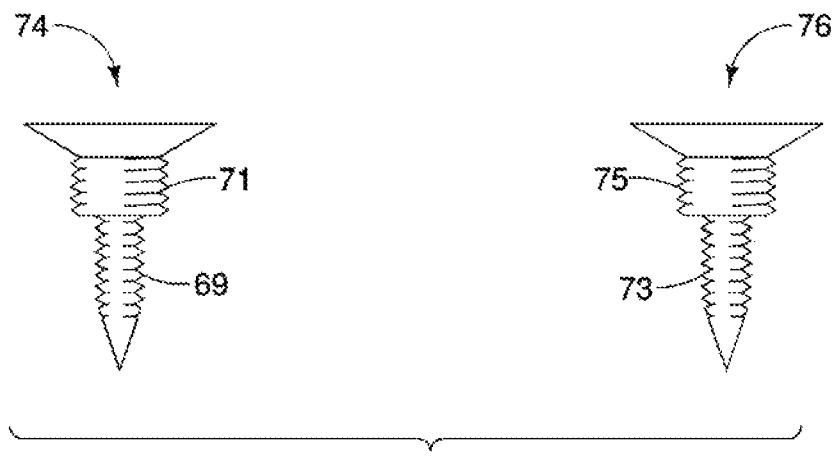
FIG. 22 shows a fastener configured to couple an orthopedic plate to one or more bone segments, wherein the fastener includes first and second threads.

As best shown in FIGS. 5a, 5b, and 6, the first and second bearings 84, 86 each include two annular ridges: an anchoring ridge 65 and a locking ridge 67. The anchoring ridge 65 defines the opening 70, 72 in each of the bearings 84, 86. As best shown in FIG. 22, the fasteners 74, 76 each include two sets of threads: anchoring threads 69, 73 and locking threads 71, 75. The anchoring threads 69, 73 are configured to mate with the anchoring ridges 65 in the first and second bearings 84, 86, respectively, while the fasteners 74, 76 are being screwed into the bone segments 28, 30. The locking threads 71, 75 are configured to mate with the locking ridge 67 when the fasteners 74, 76 are substantially or completely screwed down into the bone segments 28, 30 so as to prevent the bearings from rotating with respect to the plate portion 68. More specifically, the diameter of the locking threads 71, 75 is sized so as to cause the bearings 84, 86 to expand and form a friction engagement with the plate portion 68. The bearings 84, 86 are able to rotate with respect to the plate portion 68 except when the locking threads 71, 75 cause the bearings 84, 86 to expand and form a friction engagement with the plate portion 68. The locking feature of the fasteners 74, 76 make it easier and more effective for the medical professional to "float" the orthopedic plate 14 above the bone segments 28, 30 (i.e., to space the plate 14 apart from the bone segments 28, 30). The locking feature of the fasteners 74, 76 also may improve or stabilize the connection between the bone segments 28, 30, even when a jig 12 is not being used. The locking feature also prevents or minimizes undesired rotation the bearings 84, 86 after the plate 14 has been installed.

Referring to FIGS. 5a and 5b, the bearings 84, 86 each include an outer surface 88, 90 that is eccentric to the inner surface (e.g., the anchoring ridge 65) of the bearing 84, 86. In other words, the outer surface 88, 90 of the bearings 84, 86 and the anchoring ridge 65 each generally define circles that have different centerpoints. As a result, the distance 80 is adjusted as one of the bearings 84, 86 is rotated with respect to the frame portion 68. A medical professional is able to use the orthopedic plate 14 to cause the first and second bone segments 28, 30 to dynamically compress, or cause the bone segments 28, 30 to come into contact with each other, and potentially promote biological healing.

Figure 15:
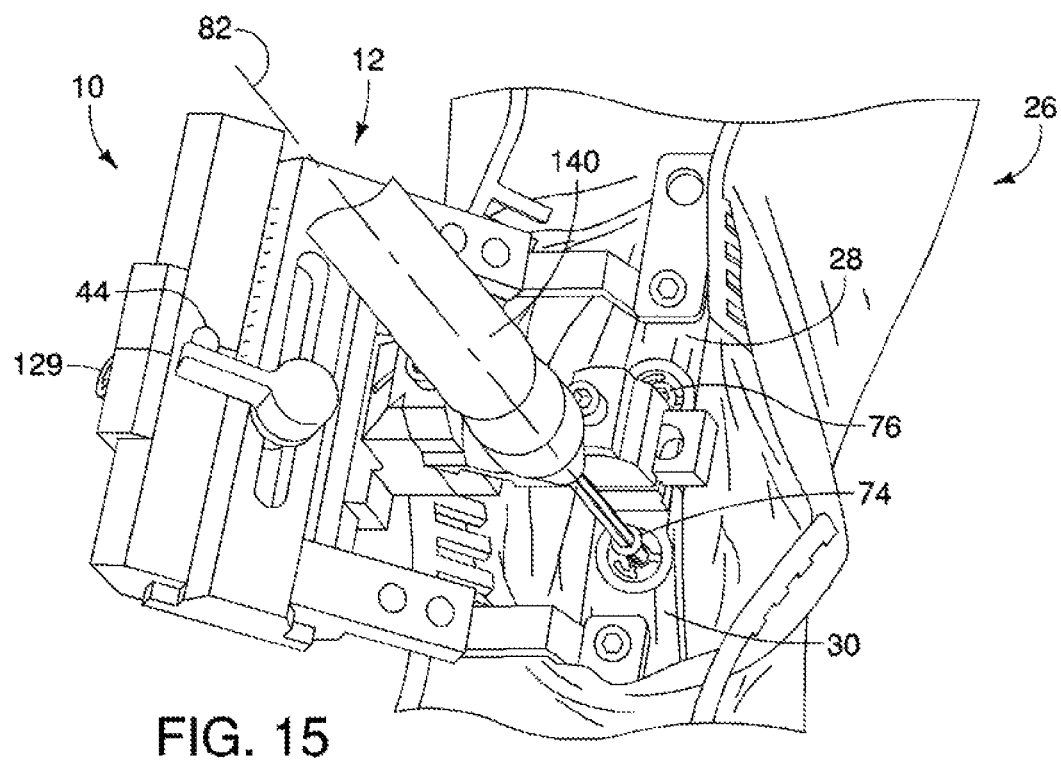
FIG. 15 shows the orthopedic device shown in FIG. 7, where a medical professional is securing the orthopedic plate to the first and second bone segments.

The plate adjustment mechanism 78 shown in the figures is configured to be able to adjust the distance 80 while the orthopedic plate 14 is spaced apart from at least one of the first and second bone segments 28, 30, as is measured generally along a fastener axis 82 (FIG. 15). In other words, the orthopedic plate 14 does not need to abut the bone segments 28, 30 to be able to adjust the distance 80, thereby permitting dynamic compression of the bone segments 28, 30 while minimizing, reducing, or avoiding distortion to the bone segments 28, 30 by the orthopedic plate 14. Utilizing the orthopedic plate 14 in this manner may be particularly advantageous where the bone segments 28, 30 are uneven along the length of the orthopedic plate 14. However, the orthopedic plate 14 is also usable and adjustable when it is abutting the bone segments 28, 30. In some cases, such as where the bone segments 28, 30 are relatively flat, it may be desirable for the orthopedic plate 14 to abut the bone segments 28, 30.

As is illustrated in FIGS. 5a and 5b, the distance 80 is largest (and the orthopedic plate 14 offers the least amount of compression) when the first and second bearings 84, 86 are each rotated such as to be in a non-compressed position 94 (i.e., where the centerpoints of the first and second bearings 84, 86 are furthest from each other). Conversely, the distance 80 is smallest (and the orthopedic plate 14 offers the maximum amount of compression) when the first and second bearings 84, 86 are each rotated such as to be in a compressed position 96 (i.e., where the centerpoints of the first and second bearings 84, 86 are closest to each other). Each of the first and second bearings 84, 86 defines a compression adjustment distance 98. The compression adjustment distance 98 is the distance measured along the longitudinal axis of the orthopedic plate 14 between the centerpoint of a bearing in the non-compressed position 94 and the compressed position 96. The distance 80 is therefore adjustable by an amount equal to the compression adjustment distance 98 of the first bearing 84 plus the compression adjustment distance 98 of the second bearing 86. In the embodiment shown in FIGS. 5a and 5b, the orthopedic plate 14 has a compression adjustment distance of approximately 1.5 millimeters, thereby allowing a medical professional to adjust the distance 80 of the orthopedic plate 14 by approximately 3.0 millimeters.

Another advantage to the orthopedic plate 14 shown in FIGS. 5a and 5b is that it allows a medical professional to adjust a horizontal distance (i.e., the distance 80) of the first and second fasteners 74, 76 independently of a vertical positioning (i.e., the position of the fasteners 74, 76 along the fastener axis 83) of the first and second fasteners 74, 76. This configuration allows a medical professional to have more control over the position (both horizontally and vertically) of the orthopedic plate 14 when coupling the same with the first and second bone segments 28, 30.

Figure 8:
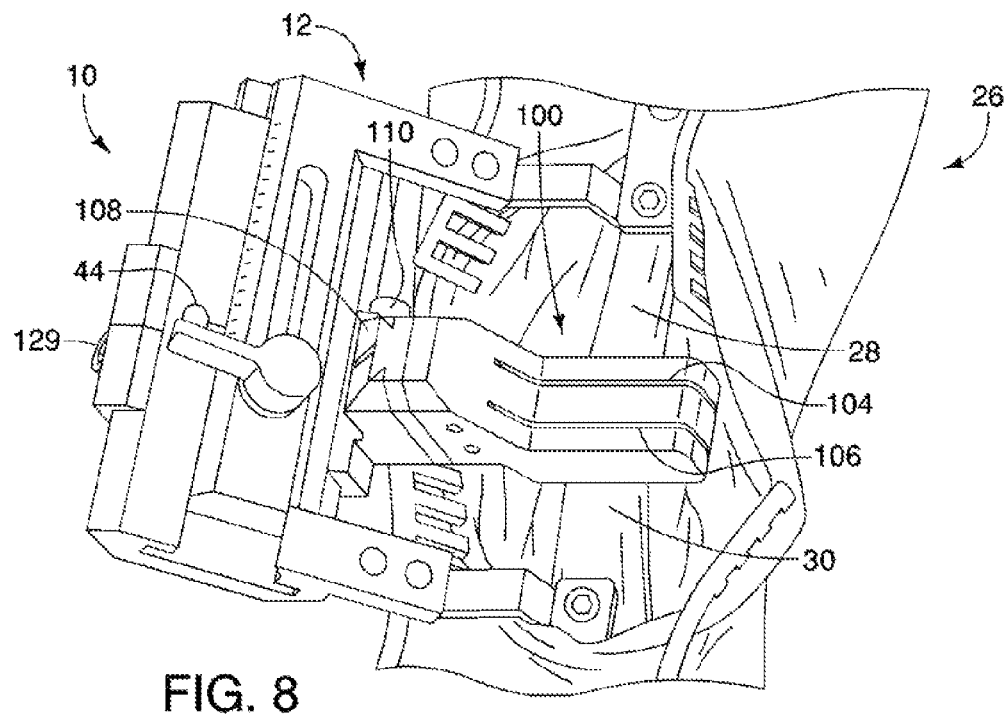
FIG. 8 shows the orthopedic device shown in FIG. 7, further including a cutting guide coupled with the jig.

The orthopedic device 10 shown in the figures also includes a cutting guide 100 coupled with the jig 12 and configured to guide a surgical saw 102 or other cutting instrument. For example, the cutting guide 100 has a pair of cutting slots 104, 106 configured to receive the surgical saw 102 and allow a medical professional to cut through the bone segments 28, 30 in a relatively straight line by following the slots 104, 106. Often times, a medical professional will desire or need to cut opposing faces of bone segments 28, 30 so as to create two complimentary surfaces that will easily and effectively achieve a union through normal biological healing. It is often advantageous for the complimentary surfaces to be flat surfaces that are generally perpendicular to the longitudinal axis of the bone(s). The cutting guide is adjustable along the y-axis 54 (FIG. 1) by way of a tab-slot connection 108 and a securing pin 110 (FIG. 8). The cutting guide is adjustable along the x-axis 62 (FIG. 1) by way of the jig adjustment mechanism 34 (FIG. 1).

Figure 9:
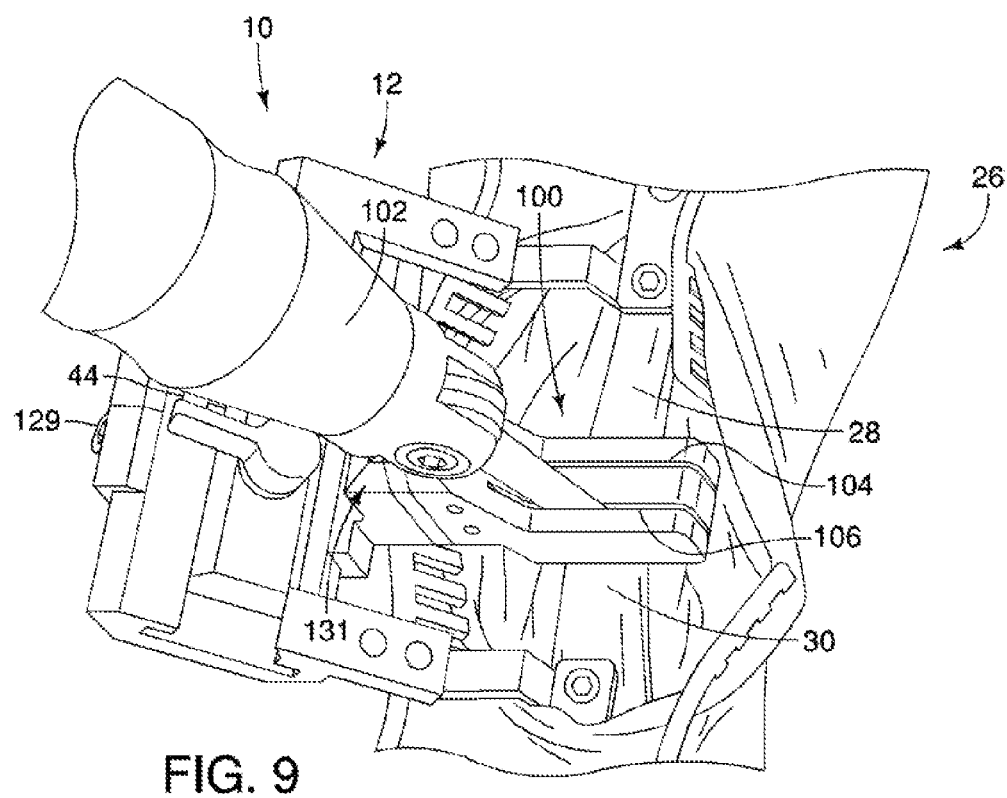
FIG. 9 shows the orthopedic device shown in FIG. 7, further including a surgical saw received within a slot of the cutting guide.

For illustrative purposes, a method of coupling first and second bone segments 28, 30 of a patient's body 26 is herein described. A medical professional (generally designated by numeral 120 in FIG. 11) makes an incision in the patient's body 26 and exposes the bone segments 28, 30 to be coupled via clamps 122, 124. As shown in FIG. 7, the medical professional couples the first arm 20 of the jig 12 with the first bone segment 28 and couples the second arm 24 of the jig 12 with the second bone segment 30 by using fasteners 126, 128. Turning to FIGS. 8 and 9, the medical professional then couples the cutting guide 100 with the jig 12 to facilitate cutting at least one of the first and second bone segments 28, 30 with the surgical saw 102. For example, the cutting guide 100 may be coupled with the jig 12 via a setscrew 129 (FIGS. 2, 9) and a dovetailed holding clamp 131 (FIG. 9). The cutting slots 104, 106 shown in the figures are approximately 3.0 millimeters apart from each other, but may have any suitable distance therebetween. Also, the medical professional can adjust the distance between the two cuts by making a first cut in the first bone segment 28 and then horizontally adjusting the position of the cutting guide 100 via the securing pin 110. The medical professional then decouples the cutting guide 100 from the jig 12.

Figure 10:
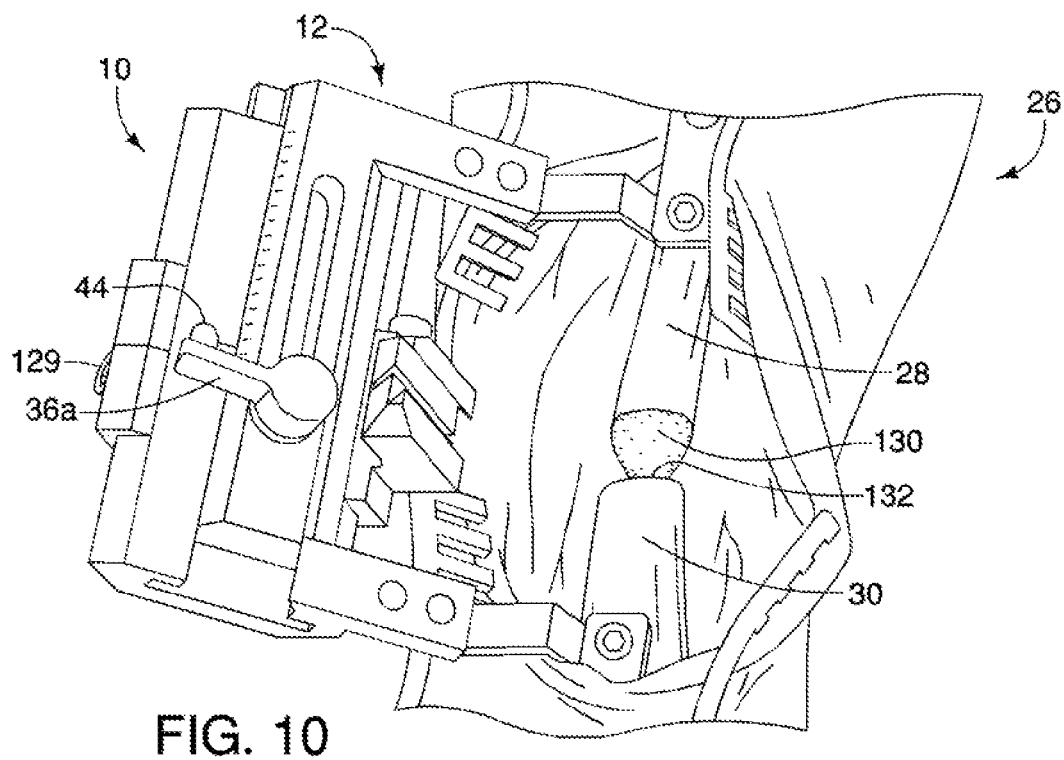
FIG. 10 shows the orthopedic device shown in FIG. 7, where portions of the first and second bone segments have been removed to form complimentary bonding surfaces.
Figure 11:
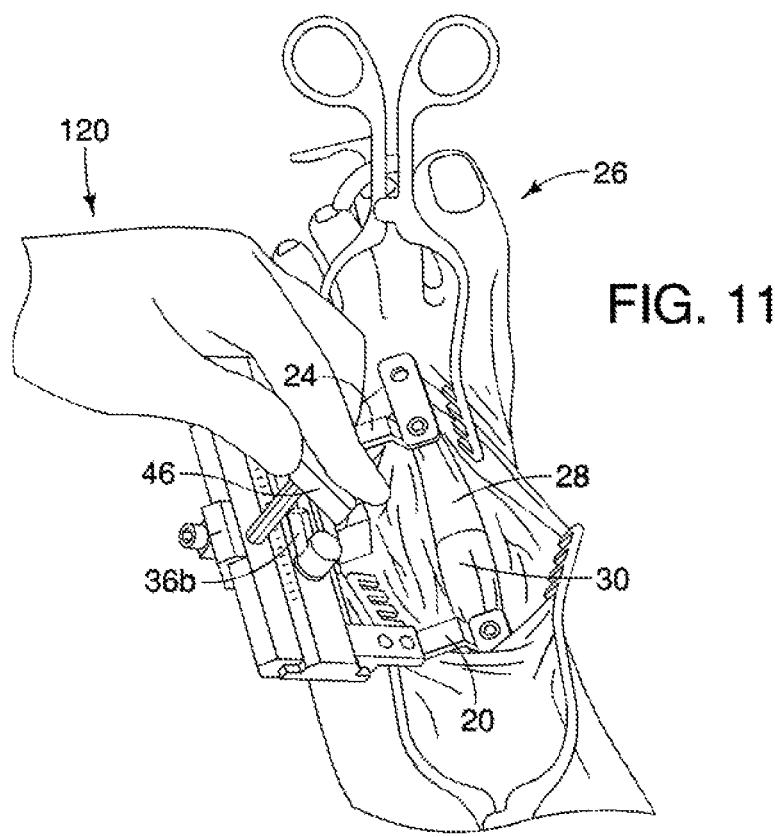
FIG. 11 shows the orthopedic device shown in FIG. 7, where a medical professional is adjusting the position of the jig first arm with respect to the jig second arm, thereby adjusting the position of the first bone segment with respect to the second bone segment.
Figure 12:
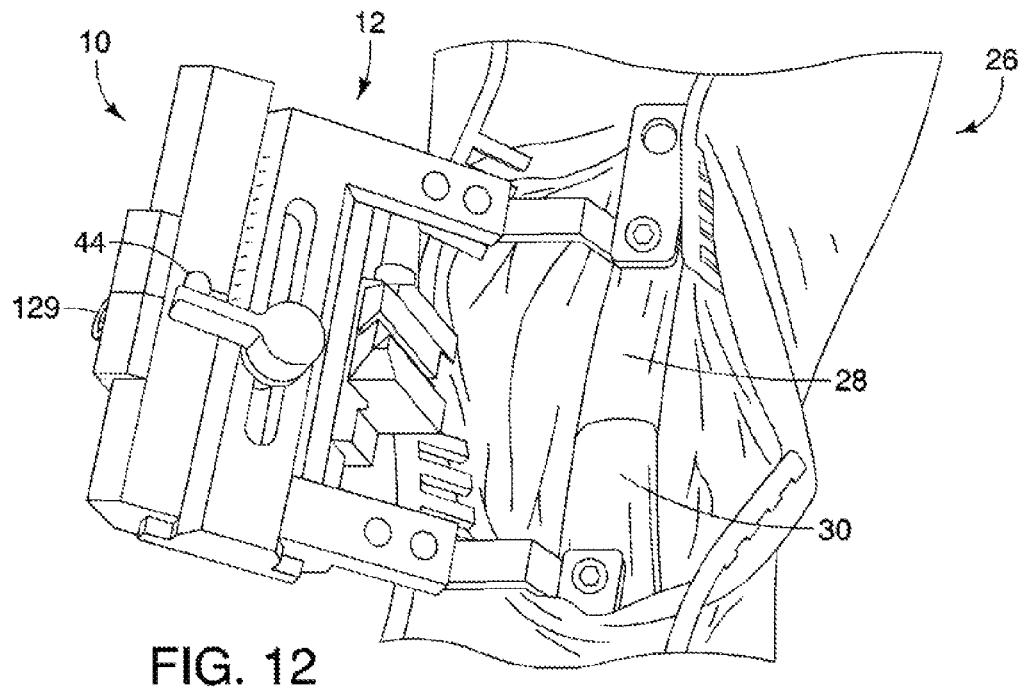
FIG. 12 shows the orthopedic device shown in FIG. 7, where the medical professional has adjusted the position of the jig first arm with respect to the jig second arm such that the first and second bone segments are abutting each other.
Figure 13:
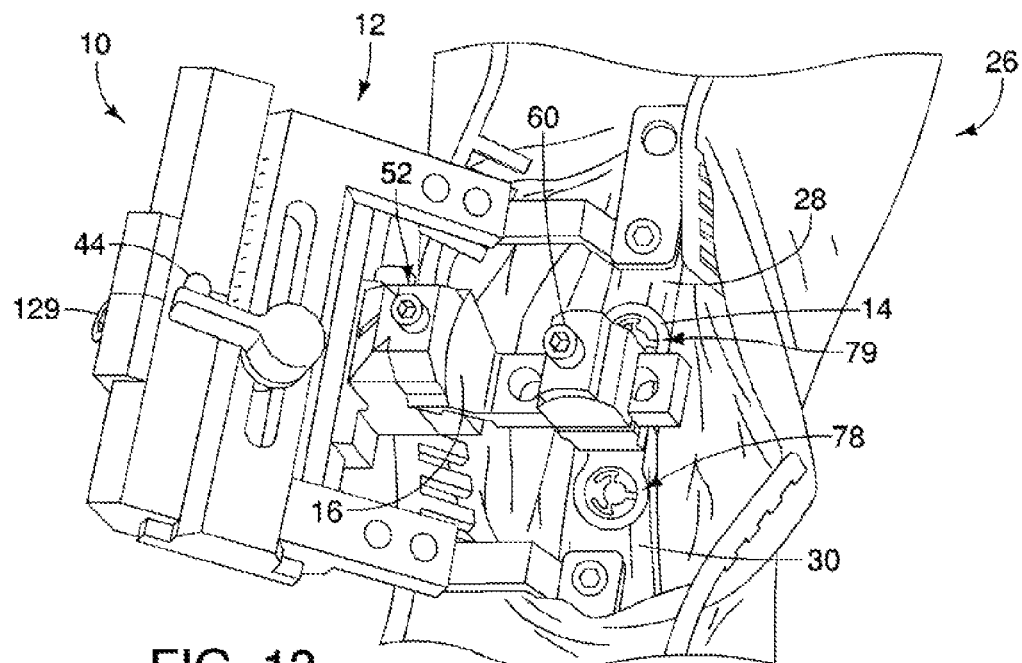
FIG. 13 shows the orthopedic device shown in FIG. 7 coupled with a plate holding mechanism, where the plate holding mechanism is configured to position an orthopedic plate with respect to the first and second bone segments.

As shown in FIG. 10, after cutting the bone segments 28, 30 preferably have flat, complimentary surfaces 130, 132 that will promote union when said surfaces are compressed together. As shown in FIG. 11, with the locking key 36 in the unlocked position 36b, the medical professional 120 rotates the adjustment key 46 so as to move the first and second arms 20, 24 with respect to each other. For example, the medical professional 120 rotates the adjustment key 46 until the bone segments 28, 30 are in contact with each other or close to being in contact with each other. The medical professional may also, or alternatively, adjust the distance between the bone segments 28, 30 by unlocking the locking key 36 and manually pressing together or pulling apart the first and second portions of the jig 12.

Once the arms 20, 24 of the jig 12 are positioned as desired, the medical professional then moves the locking key 36 into the locked position 36a (FIG. 12) thereby coupling the plate holding mechanism 16 with the jig 12. The medical professional can adjust the horizontal or vertical position of the orthopedic plate 14 via the vertical adjustment mechanism 52 and the horizontal adjustment mechanism 60, respectively.

Figure 14:
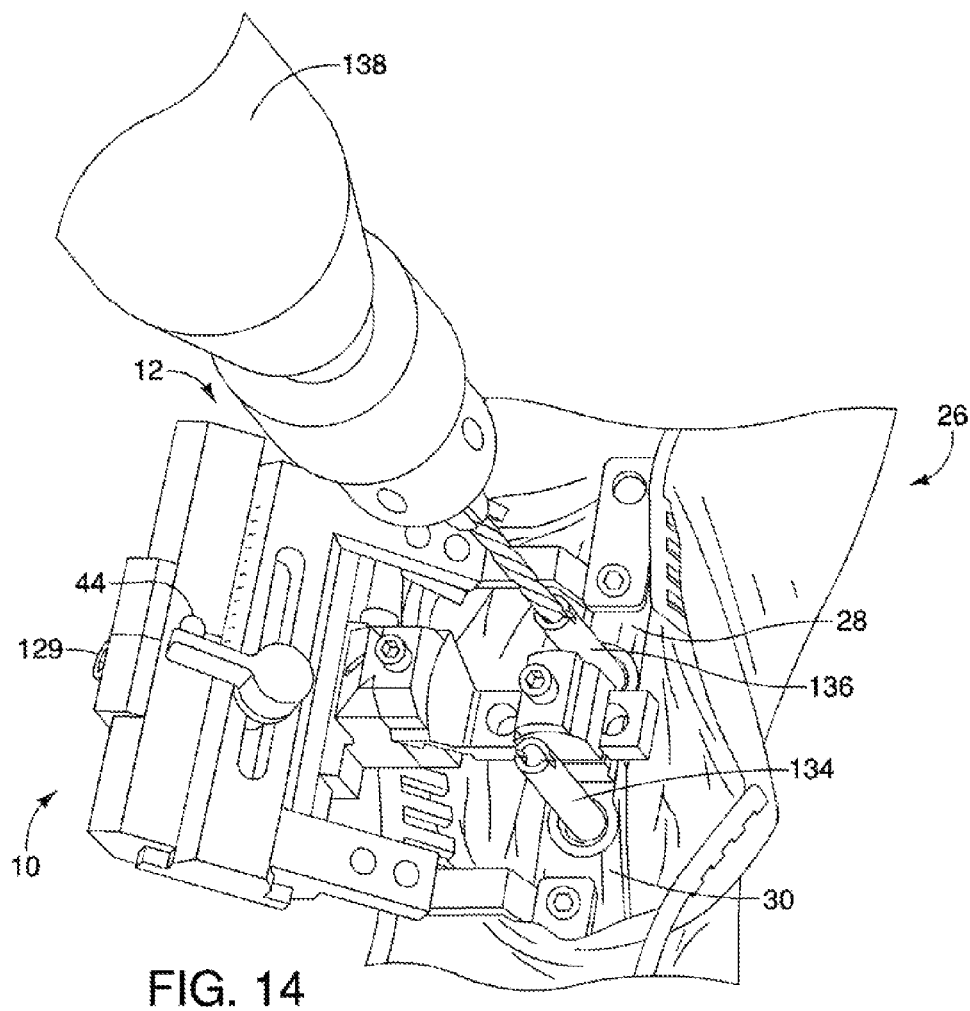
FIG. 14 shows the orthopedic device shown in FIG. 7, further including drill guides coupled with the orthopedic plate and where the medical professional is drilling along the drill guides and into the first and second bone segments.

As shown in FIG. 14, once the orthopedic plate 14 is in the desired position with respect to the bone segments 28, 30, the medical professional secures drilling guides 134, 136 to the orthopedic plate 14 and uses a surgical drill 138 to drill through the drill guides 134, 136 and into the bone segments 28, 30. The drilling guides 134, 136 shown in the figures are perpendicular to the orthopedic plate 14 and are coupled therewith by a threaded connection. Specifically, the drilling guides 134, 136 mate with the locking ridge 67. The inside diameter of the drilling guides 134, 136 corresponds to the diameter of the first and second openings 70, 72 (i.e., the diameter defined by the anchoring ridge) to assist with alignment of the drill bit as it creates holes in the bone segments 28, 30. The medical professional then removes the drilling guides 134, 136 from the orthopedic plate 14 and, as is shown in FIG. 15, secures a first portion of the orthopedic plate 14 to the first bone segment 28 and secures a second portion of the orthopedic plate 14 to the second bone segment 30. For example, the medical professional shown in FIG. 15 is securing the orthopedic plate 14 to the bone segments 28, 30 via the fasteners 74, 76 and a screwdriver 140.

When the fastener heads are flush with the bearings, the bearings outwardly expand, thereby locking the bearings in place with respect to the orthopedic plate frame portion and prevent rotation of the bearing. When the bearing is expanded (and thus locked) it forms an interference fit with the orthopedic plate frame portion, thereby substantially or completely preventing the bearing from back spinning into an uncompressed position under physiologic loads. The bearings 84, 86 include bearing key holes 148, 150 that facilitate rotation of the bearings 84, 86, as well as facilitate compression of the bone segments 28, 30, as will be described in more detail below. In other words, the first and second bearings 84, 86 are configured to facilitate rotation of the bearings with respect to the frame portion 68 while the fasteners 74, 76 are received within the first and second openings 70, 72, respectively.

Figure 16:
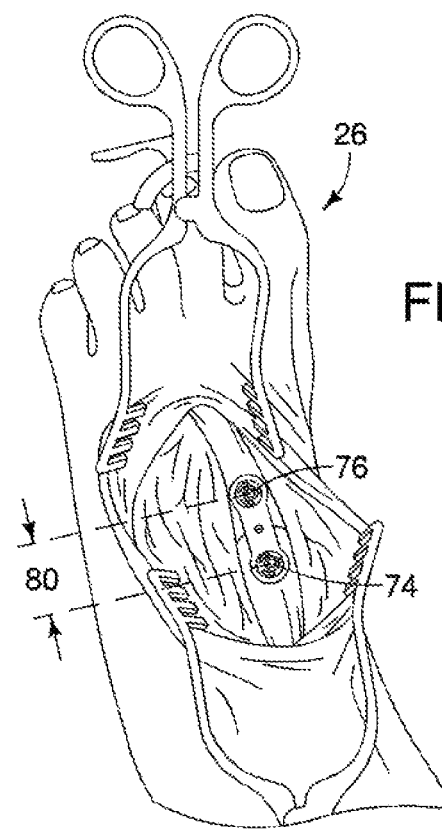
FIG. 16 shows the orthopedic plate shown in FIG. 15, where the jig and orthopedic plate holding mechanism have been decoupled from the orthopedic plate.
Figure 17:
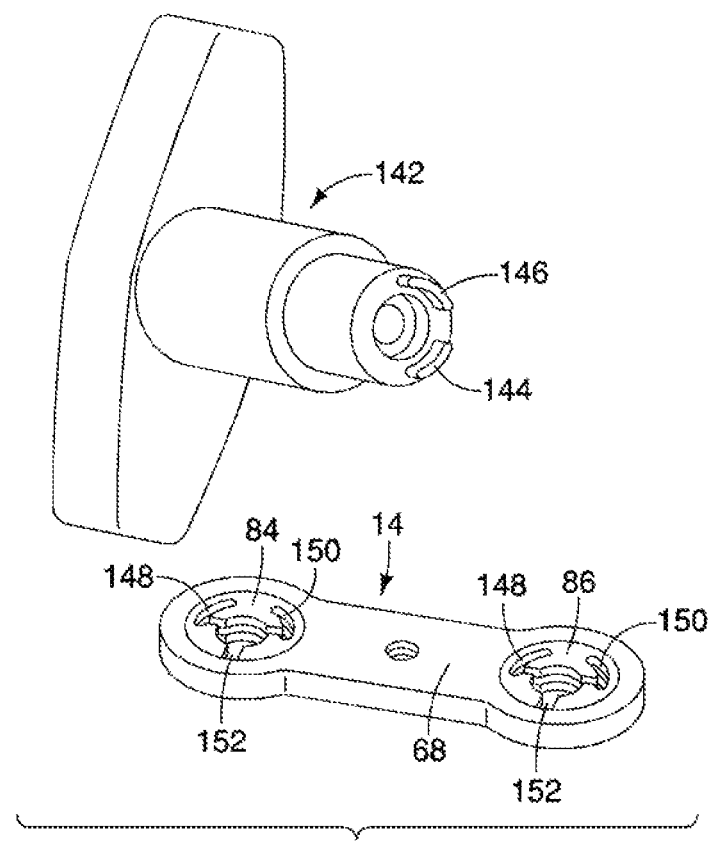
FIG. 17 shows an isometric view of the orthopedic plate shown in FIG. 15 and a plate adjustment mechanism configured to mate with the orthopedic plate and adjust the position of bearings therein.
Figure 18:
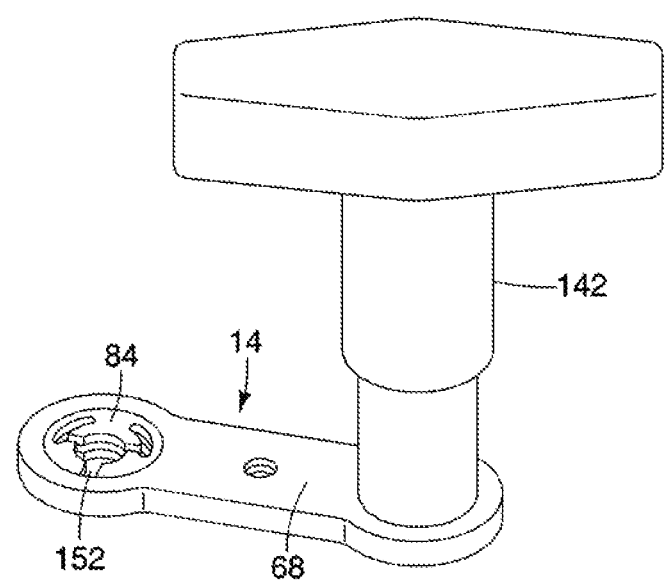
FIG. 18 shows an isometric view of the orthopedic plate and plate adjustment mechanism shown in FIG. 17, where the orthopedic plate and plate adjustment mechanism are mated with each other.

Next, the plate holding mechanism 16 is decoupled from the orthopedic plate 14 and the jig is decoupled from the bone segments 28, 30. The medical professional then, if desired, uses the first and/or second plate adjustment mechanisms 78, 79 to adjust the distance 80 between the first and second bone segments 28, 30. For example, as shown in FIGS. 16-18, the medical professional first loosens the fastener by at least one-half of a turn to unlock the bearing with respect to the frame portion. The medical professional may then use a bearing key 142 to rotate the first and/or second bearings 84, 86 with respect to the frame portion 68 of the orthopedic plate 14. The bearing key 142 shown in the figures includes a first key tooth 144 and a second key tooth 146 that correspond to and fit within the bearing key holes 148, 150, respectively. The bearing key holes 148, 150 are spaced apart and shaped so as to permit the medical professional to apply a torque force thereon and rotate the bearings 84, 86, thereby permitting dynamic compression of the bone segments 28, 30. For example, the bearing key holes 148, 150 shown in the figures are generally opposite each other on the bearings 84, 86. Additionally, the bearing key holes 148, 150 shown in the figures have a generally curved shape to promote a torque force on the bearings 84, 86.

The desired distance 80 may vary depending on various circumstances, but it is typically 0.00 to 0.05 millimeters. After rotationally adjusting the bearings and obtaining a desired distance 80 and, if applicable, compression force, the medical professional tightens the fasteners so the fastener heads are flush with the bearings and the bearings are locked with respect to the frame portion. The fastener heads shown in the figures are conical, but they may be flat or any other shape.

Figure 19:
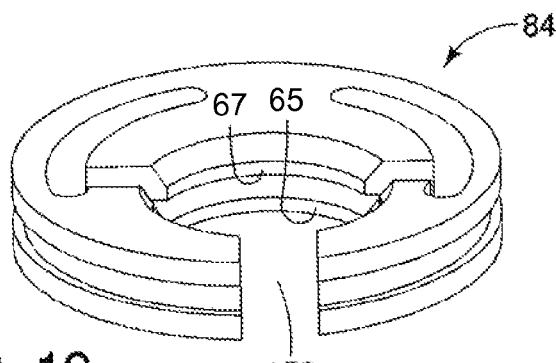
FIG. 19 shows an isometric view of the underside of the bearing for the orthopedic plate shown in FIG. 17.
Figure 20:
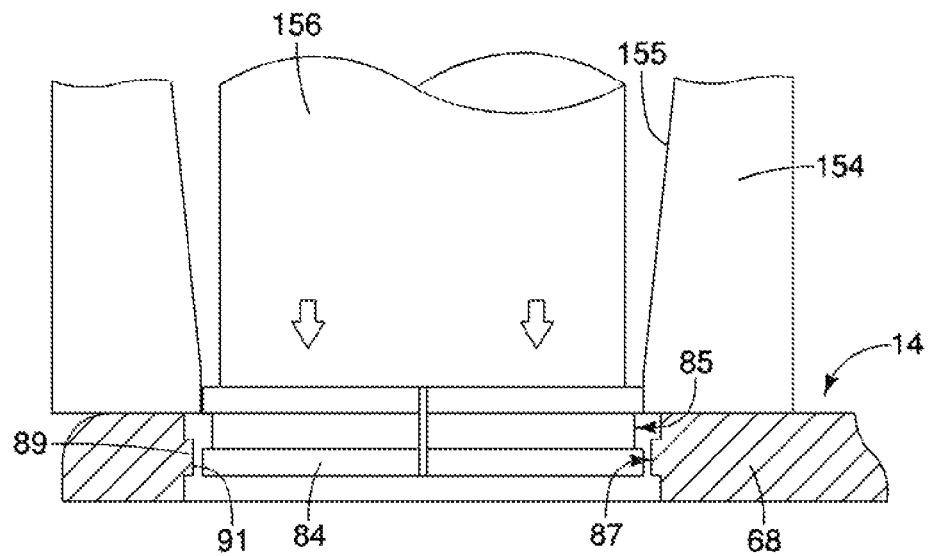
FIG. 20 shows the bearing being coupled with the orthopedic plate frame.
Figure 21:
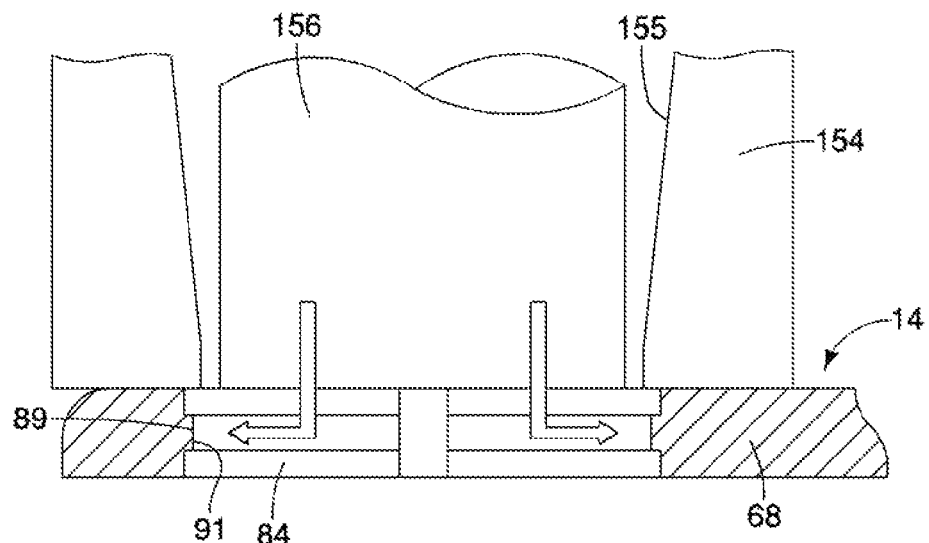
FIG. 21 shows the bearing coupled with the orthopedic plate frame.

As shown in FIGS. 19-21, the bearing 84 may be coupled with the frame portion 68 of the orthopedic plate 14 via a spring connection. For example, the bearing has a notch 152 that allows the bearing to act like a C-shaped spring and compress and expand depending on the lateral force applied. The bearing 84 is inserted within a guide sleeve 154 that is coupled with or positioned flush with the frame portion 68 of the orthopedic plate 14. A punch mechanism 156 pushes down on the bearing 84 and forces it downward in the guide sleeve 154, until the bearing 84 is in a desired position with respect to the frame portion 68. For example, in the embodiment shown in the figures, the bearing 84 is in the desired location when an outer surface 85 of the bearing contacts an inner surface 87 of the frame portion 68. More specifically, in the embodiment shown in the figures, the bearing 84 is in the desired location when it snaps into place in the frame portion 68. The outer surface 85 of the bearing 84 includes a notch 89 that is configured to mate with a ring 91 in the inner surface 87 of the frame portion 68 to secure the bearing 84 with respect to the frame portion 68. The guide sleeve 154 shown in the figures includes an inner wall 155 that is tapered inwardly to increase the compression of the bearing 84 as it is forced downward by the punch mechanism 156.

Figure 23:
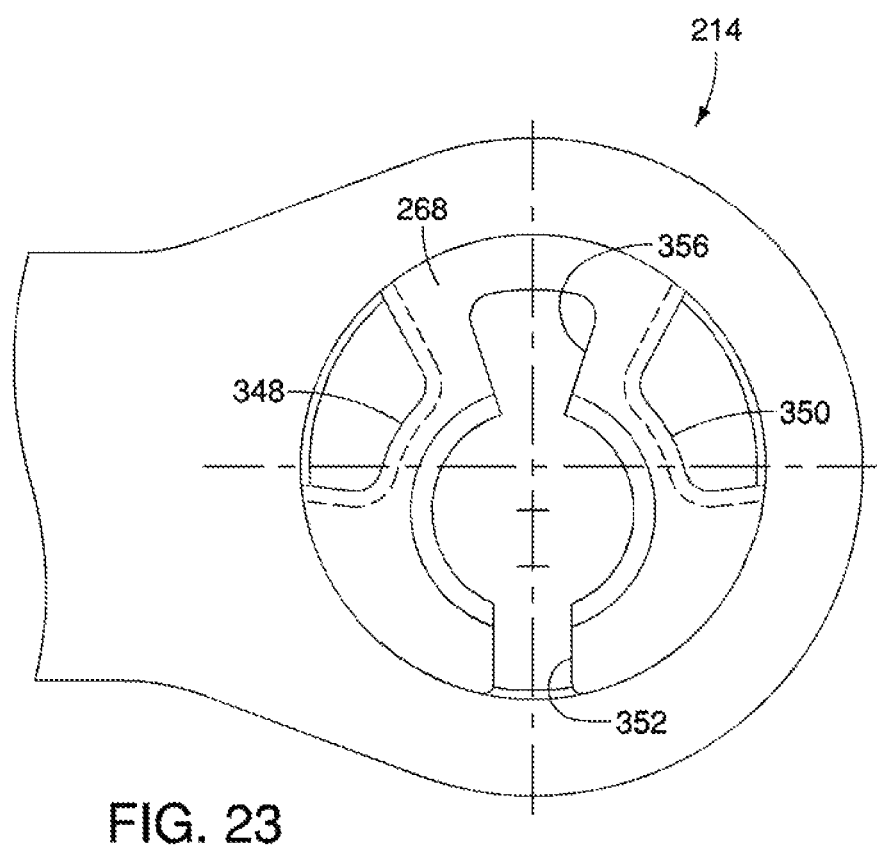
FIG. 23 shows an alternative embodiment of an orthopedic plate embodying principles of the present invention.

In one alternative embodiment, as shown in FIG. 23, an orthopedic plate 214 is provided having a bearing 268 with a first notch 352 in one portion of the bearing 268 and a second notch 356 diametrically opposed to the first notch 352 to alter the spring coefficient of the bearing 268 compared to the bearing shown in the prior figures. The bearing key holes 348, 350 are also larger than those shown in the prior figures and define portions of the outer surface of the bearing 268.

Figure 24:
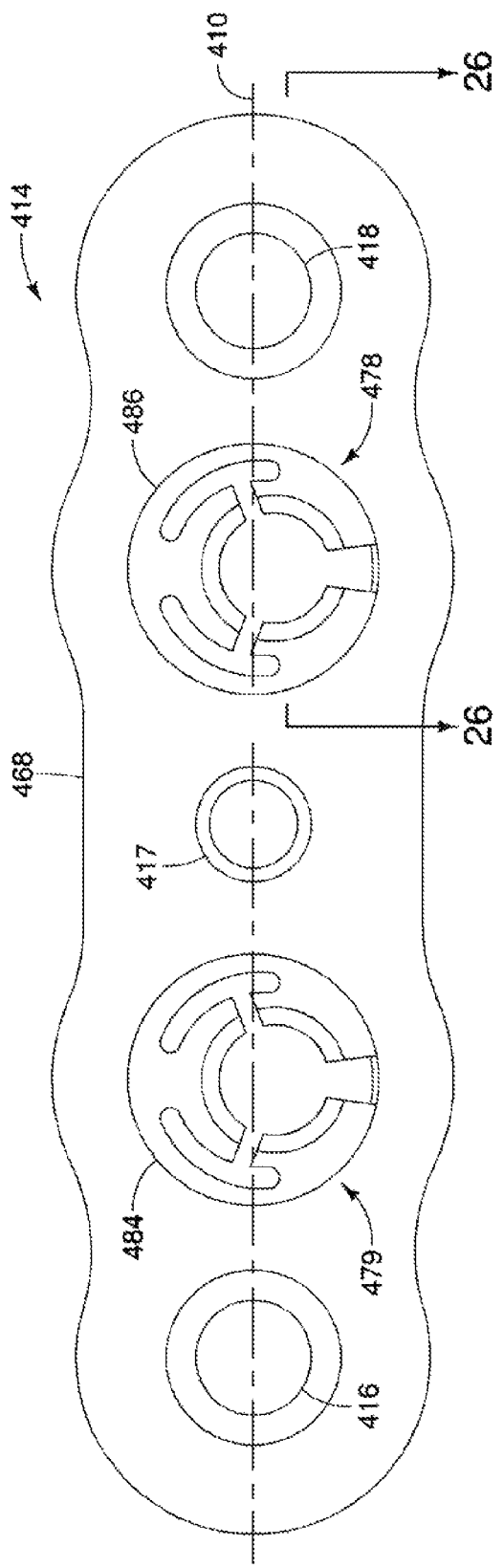
FIG. 24 is another alternative embodiment of an orthopedic plate embodying principles of the present invention.
Figure 26:
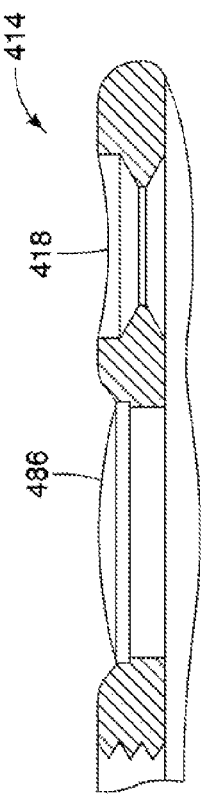
FIG. 26 is a cross-sectional view of the orthopedic plate shown in FIG. 24 taken along line 26-26.
Figure 25:
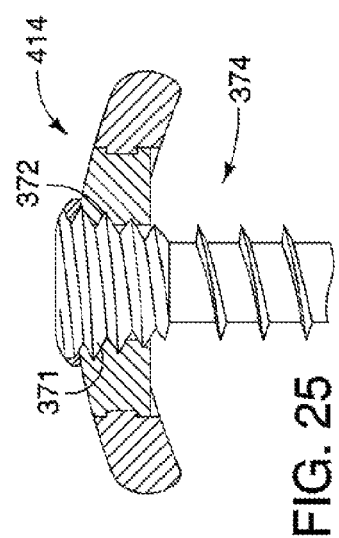
FIG. 25 is a fastener coupled with the orthopedic plate shown in FIG. 24.

In another alternative embodiment, as shown in FIGS. 24-26, an orthopedic plate 414 is provided having a frame portion 468 and first and second plate adjustment mechanisms 478, 479 that are each configured to adjust a distance between first and second fasteners received within the plate adjustment mechanisms 478, 479. The plate adjustment mechanisms 478, 479 shown in the figure include first and second bearing 484, 486 that are each rotatable with respect to the frame portion 468. The frame portion 468 is generally curved along a longitudinal axis 410 so as to match the curvature of a bone. The orthopedic plate 414 also defines openings 412, 413, 414 for receiving fasteners and thereby further securing the orthopedic plate 414 to the bone. Alternatively, the opening 413 may be used as a connection point to a jig 12 or other device.

As shown in FIG. 27, in an alternative design, fasteners 174, 176 include a locking head 171, 175 configured to be received by the locking ridge 67 of the bearings. The locking head 171, 175 is tapered so as to increase the radially expansion of the diameter of the bearings as the locking head 171, 175 is driven downward with respect to the orthopedic plate. As with the locking threads 71, 75, the locking heads 171, 175 are configured to mate with the locking ridge 67 when the fasteners 174, 176 are substantially or completely screwed down into the bone segments 28, 30 so as to prevent the bearings from rotating with respect to the plate portion 68. More specifically, the diameter of the locking threads 171, 175 is sized so as to cause the bearings 84, 86 to expand and form a friction engagement with the plate portion 68. The bearings 84, 86 are able to rotate with respect to the plate portion 68 except when the locking threads 171, 175 cause the bearings 84, 86 to expand and form a friction engagement with the plate portion 68.

FIG. 25 shows another alternative design for a fastener 374, where a locking head 371 is tapered so as to increase the radially expansion of the diameter of the bearings as the locking head 371 is driven downward with respect to the orthopedic plate 414. Additionally, the locking head 371 includes threads 372 configured to mate with threads in the orthopedic plate 414.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

The invention claimed is:

1. An orthopedic plate assembly, comprising:
a frame portion;
a bearing rotatably coupled with the frame portion, wherein the bearing defines an opening configured to receive a fastener for fastening the frame portion to a body, wherein the bearing includes an outer surface that is eccentric to the opening such that a position of the opening with respect to the frame portion is adjustable as the bearing rotates and wherein the bearing includes at least a first ridge with an annular shape projecting into the opening to provide a first inner diameter in the opening and a second ridge with an annular shape projecting into the opening to provide a second inner diameter in the opening that is larger than said first inner diameter, wherein said opening provides a longitudinal direction of travel for said fastener, with the first inner diameter located in a first plane and the second inner diameter located in a second plane, the first plane and the second plane each extending perpendicularly to said longitudinal direction of travel and being spaced from one another along said longitudinal direction of travel; and
a fastener receivable in the opening for fastening the frame portion to the body, wherein the fastener includes a tapered head section with threads, and wherein the fastener is advanceable in the opening in a direction from the second ridge toward the first ridge such that contact between the fastener and the bearing causes the bearing to radially expand and become non-rotatably locked in the frame portion in a manner that includes the tapered head section contacting the second ridge for preventing rotation of the bearing in the frame portion.

2. An orthopedic plate assembly as in claim 1, further comprising a second bearing rotatably coupled with the frame portion, wherein the second bearing defines a second opening configured to receive a second fastener for further fastening the frame portion to the body, wherein the second bearing includes an outer surface that is eccentric to the second opening.

3. An orthopedic plate assembly as in claim 1, wherein the bearing being rotatably coupled with the frame portion maintains the bearing at a set vertical position in the frame portion, the bearing being rotatable in the frame portion when located at said set vertical position.

4. An orthopedic plate assembly, comprising:
a frame portion;
a bearing rotatably coupled with the frame portion, wherein the bearing defines an opening having a central longitudinal axis and being configured to receive a fastener for fastening the frame portion to a body, wherein the bearing includes an outer surface that is eccentric to the opening such that a position of the opening with respect to the frame portion is adjustable as the bearing rotates and wherein the bearing includes at least a first ridge with an annular shape projecting into the opening to provide a first inner diameter in the opening and a second ridge with an annular shape projecting into the opening to provide a second inner diameter in the opening that is larger than said first inner diameter, wherein said opening provides a longitudinal direction of travel for said fastener, with the first inner diameter located in a first plane and the second inner diameter located in a second plane, the first plane and the second plane each extending perpendicularly to said longitudinal direction of travel and being spaced from one another along said longitudinal direction of travel, said first ridge having a maximum ridge height extending from a base of the first ridge toward the central longitudinal axis of said opening and said second ridge having a maximum ridge height extending from a base of the second ridge toward the central longitudinal axis of said opening, the maximum ridge height of said first ridge being greater than the maximum ridge height of said second ridge; and a fastener receivable in the opening for fastening the frame portion to the body, wherein the fastener includes a tapered head section, and wherein the fastener is advanceable in the opening in a direction from the second ridge toward the first ridge such that contact between the fastener and the bearing causes the bearing to radially expand and become non-rotatably locked in the frame portion in a manner that includes the tapered head section contacting the second ridge for preventing rotation of the bearing in the frame portion.

5. An orthopedic plate assembly as in claim 4, wherein the tapered head section includes threads.

6. An orthopedic plate assembly, comprising:
a frame portion;
a bearing rotatably coupled with the frame portion, wherein the bearing defines an opening configured to receive a fastener for fastening the frame portion to a body, wherein the bearing includes an outer surface that is eccentric to the opening such that a position of the opening with respect to the frame portion is adjustable as the bearing rotates and wherein the bearing includes at least a first ridge with an annular shape projecting into the opening to provide a first inner diameter in the opening and a second ridge with an annular shape projecting into the opening to provide a second inner diameter in the opening that is larger than said first inner diameter, wherein said opening provides a longitudinal direction of travel for said fastener, with the first inner diameter located in a first plane and the second inner diameter located in a second plane, the first plane and the second plane each extending perpendicularly to said longitudinal direction of travel and being spaced from one another along said longitudinal direction of travel; and
a fastener receivable in the opening for fastening the frame portion to the body, the fastener including a locking head, the fastener including a first set of fastener threads for entering bone and a second set of fastener threads on the locking head, wherein the fastener is advanceable in the opening in a direction from the second ridge toward the first ridge such that the locking head contacts the second ridge to radially expand the bearing for preventing rotation of the bearing in the frame portion in a manner that includes the locking head contacting the second ridge so as to be removably locked to the second ridge.

7. An orthopedic plate assembly as in claim 6, wherein the locking head includes a tapered section.

8. An orthopedic plate assembly, comprising:
a frame portion;
a self-securable bearing member snapped into place in the frame portion so as to be self-secured at a set vertical position within the frame portion, the bearing member being rotatable within the frame portion when located at said set vertical position and providing an opening through which a fastener can pass for fastening the frame portion to a body, wherein the bearing member includes at least a first annular-shaped ridge and a second annular-shaped ridge which each project into said opening, and wherein the bearing includes an outer surface that is eccentric to the opening such that a position of the opening with respect to the frame portion is adjustable as the bearing rotates; and
a fastener receivable in the opening for fastening the frame portion to the body, wherein the fastener includes a tapered head section with threads, and wherein the fastener is advanceable in the opening in a direction from the second annular-shaped ridge toward the first annular-shaped ridge such that contact between the fastener and the bearing member causes the bearing member to radially expand and become non-rotatably locked in the frame portion in a manner that includes the tapered head section contacting the second ridge for preventing rotation of the bearing member in the frame portion.

9. An orthopedic plate assembly as in claim 8, wherein the outer surface of the bearing member has only a single notch that is mated with a single ring on an inner surface of the frame portion for rotating said single notch about said single ring.

10. An orthopedic plate assembly as in claim 9, wherein said single notch is situated midway between a top surface and a bottom surface of the bearing member.

11. An orthopedic plate assembly as in claim 9, wherein the outer surface of the bearing member is flush with the inner surface of the frame portion along the entire height of said outer surface.

12. An orthopedic plate assembly as in claim 8, wherein the bearing member provides a first curved key hole and a second curved key hole spaced from one another in the bearing member, and wherein the first curved key hole and the second curved key hole are positioned between the opening and the outer surface of the bearing member and extend circumferentially around the bearing member toward one another.

13. An orthopedic plate assembly as in claim 12, wherein the first curved key hole and the second curved key hole each extend for a distance in a curved manner around the bearing member.

14. An orthopedic plate assembly as in claim 8, wherein the first annular-shaped ridge has an inner diameter that is smaller than an inner diameter of the second annular-shaped ridge.

15. An orthopedic plate assembly as in claim 14, wherein said opening provides a longitudinal direction of travel for said fastener, with the inner diameter of the first annular-shaped ridge located in a first plane and the inner diameter of the second annular-shaped ridge located in a second plane, said first plane and said second plane each extending perpendicularly to said longitudinal direction of travel and being spaced from one another along said longitudinal direction of travel.

16. An orthopedic plate assembly as in claim 8, wherein, when the bearing member is non-rotatably locked in the frame portion with the tapered head section contacting the second ridge, the fastener is movable in the opening in a direction from the first ridge toward the second ridge for unlocking the bearing member in the frame portion so as to permit rotation of the bearing member in the frame portion.

* * * * *